United States Patent [19]
Cornuejols et al.

[11] Patent Number: 5,214,578
[45] Date of Patent: May 25, 1993

[54] METHOD AND SYSTEM FOR THE CALIBRATION OF AN X-RAY SCANNER USING AN OFF-CENTERED CIRCULAR PHANTOM

[75] Inventors: Dominique Cornuejols, Palaiseau; Andrei Feldman, Paris, both of France

[73] Assignee: General Electric CGR SA, Issy les Moulineaux, France

[21] Appl. No.: 362,680

[22] Filed: Jun. 7, 1989

[30] Foreign Application Priority Data

Jun. 10, 1988 [FR] France ................ 88 07791

[51] Int. Cl.⁵ ............................ G06F 15/42
[52] U.S. Cl. ................... 364/413.13; 378/18; 378/207
[58] Field of Search ............ 364/413.13, 413.14; 378/18; 378/207; 250/252.1

[56] References Cited
U.S. PATENT DOCUMENTS

| | | | |
|---|---|---|---|
| 4,225,789 | 9/1980 | Albrecht | 378/207 X |
| 4,352,020 | 9/1982 | Horiba et al. | 378/18 |
| 4,400,827 | 8/1983 | Spears | 378/207 |
| 4,497,061 | 1/1985 | Hounsfield | 378/18 |
| 4,654,796 | 3/1987 | Takagi et al. | 364/413.15 |
| 4,663,772 | 5/1987 | Mattson et al. | 378/18 |
| 4,787,098 | 11/1988 | Silver | 378/18 |
| 4,873,707 | 10/1989 | Robertson | 378/18 |
| 4,897,788 | 1/1990 | King | 364/413.15 |
| 4,980,904 | 12/1990 | Sones et al. | 378/207 |

Primary Examiner—Roy N. Envall, Jr.
Assistant Examiner—David Huntley
Attorney, Agent, or Firm—Nilles & Nilles

[57] ABSTRACT

A method and system to calibrate an X-ray scanner uses a single circular phantom. The circular phantom is off-centered with respect to the axis of rotation of the scanner so as to introduce different paths in the phantom for each channel, depending on the angular positions of the scanner. This results in different attenuation measurements which are compared with values obtained by the computation of the path lengths which depend on the off-centered coordinates r and Φ and on the position of the scanner, thus enabling computation of the polynomial approximation coefficients to be applied to the measurements.

4 Claims, 3 Drawing Sheets

FIG_1
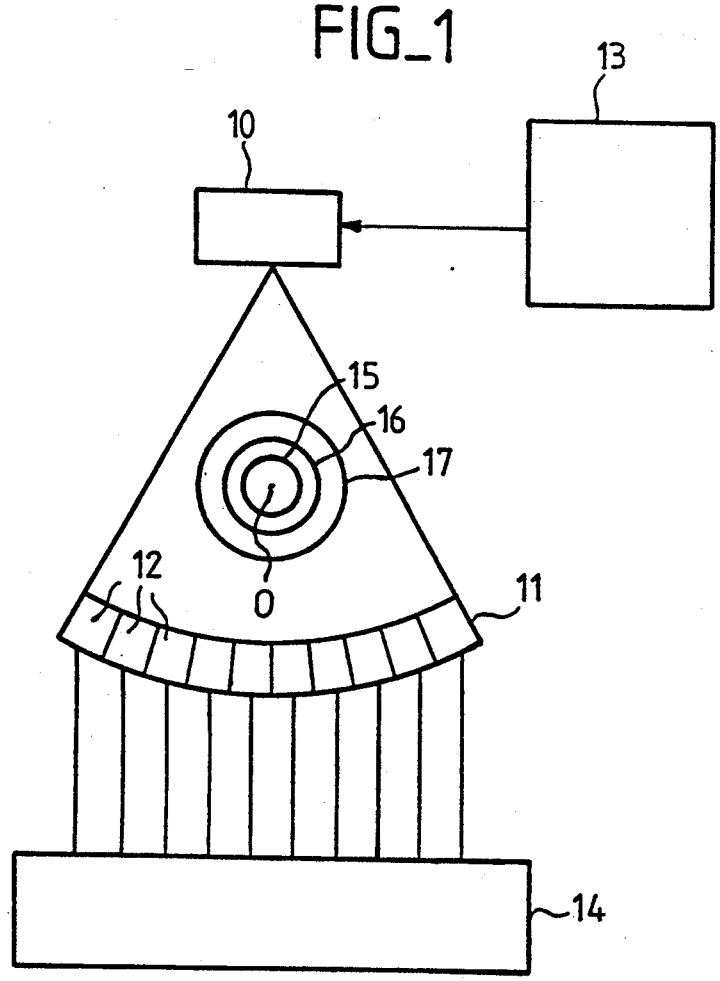
FIG_2
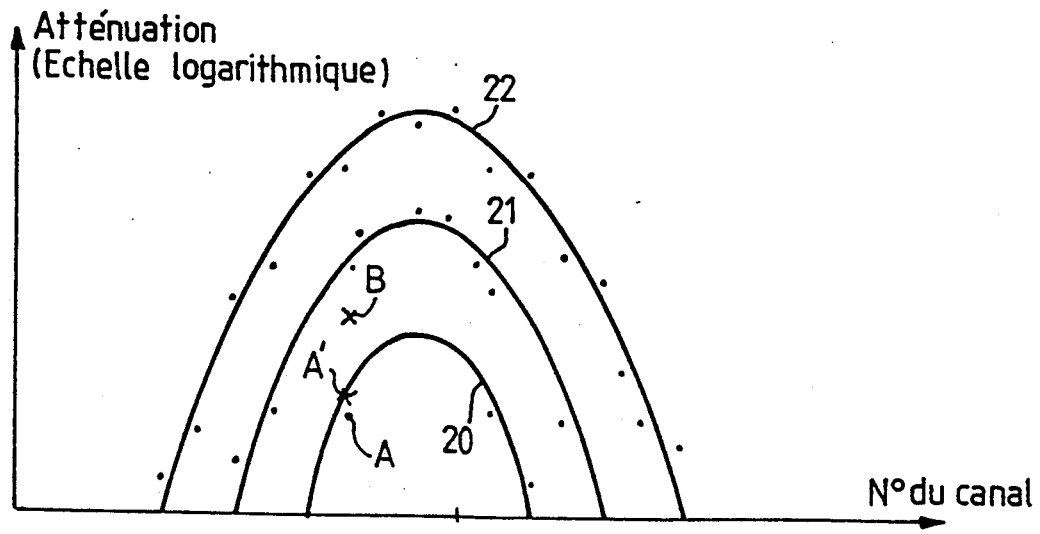
Atténuation
(Echelle logarithmique)
N° du canal

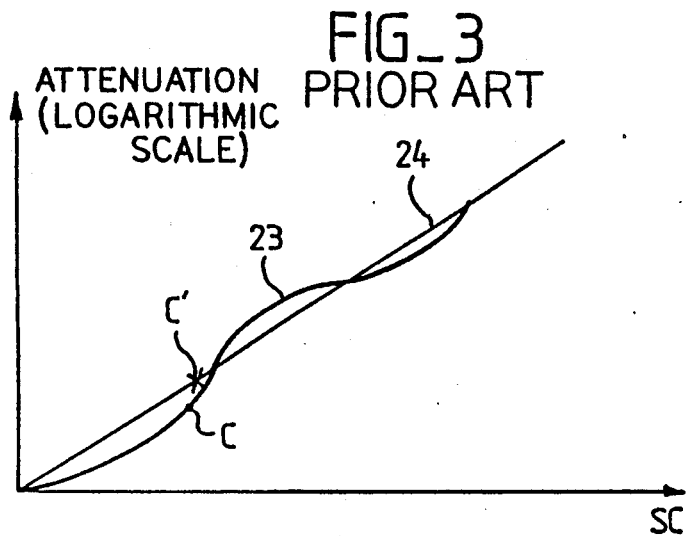
FIG_3 PRIOR ART
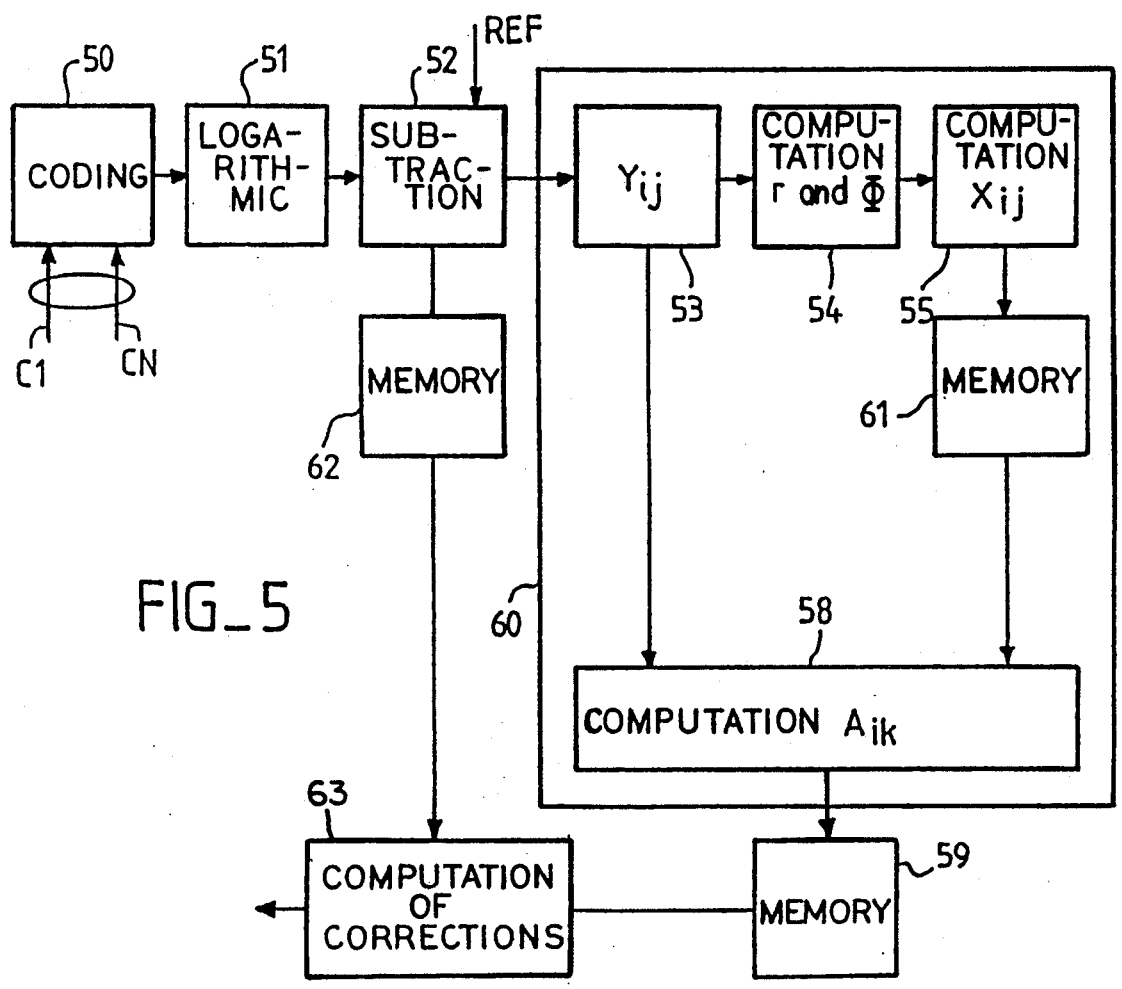
FIG_5

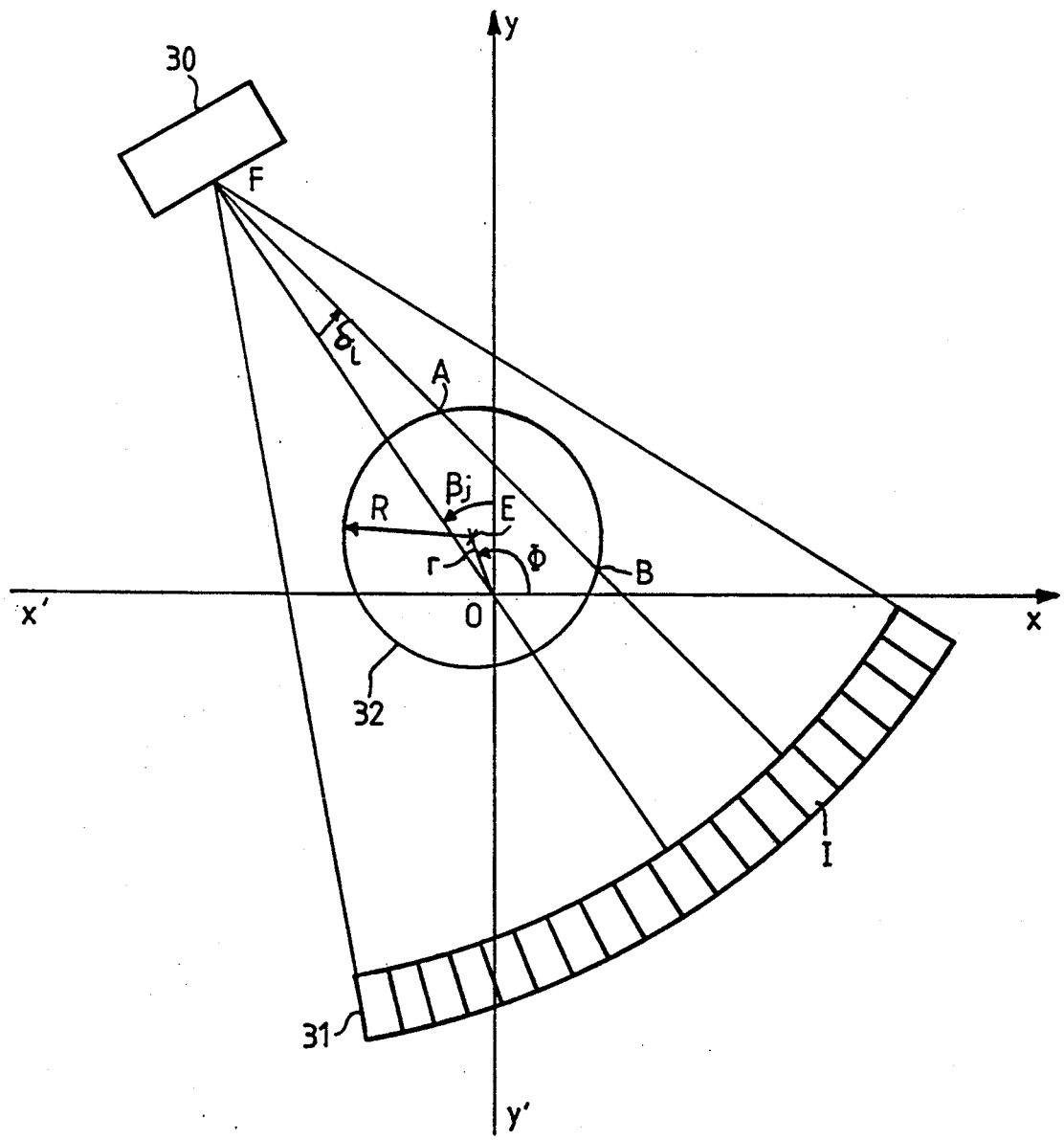
FIG_4

5,214,578

METHOD AND SYSTEM FOR THE CALIBRATION OF AN X-RAY SCANNER USING AN OFF-CENTERED CIRCULAR PHANTOM

BACKGROUND OF THE INVENTION

1. Field of the Invention

The invention concerns X-ray scanners and, more particularly, a method for the calibration of machines of this type using one or more circular phantoms which are off-centered with respect to the axis of rotation of the scanner. The invention also concerns a system which can be used to implement this method.

2. Description of the Prior Art

To examine patients, increasingly frequent use is being made of X-ray machines, called scanners, which make cross-sectional images of these patients. These machines are based on the physical phenomenon of X-ray absorption by the human body. For a monochromatic beam, this absorption is directly related to the distance x travelled by the X-rays in a homogeneous body according to the formula:

$$I = I_0 e^{-bx}$$

a formula wherein:

$I_o$ is the intensity of the radiation entering the human body,

I is the intensity of the radiation leaving the human body, b is a coefficient of X-ray absorption depending on the body through which the radiation flows.

In a logarithmic measurement scale, the attenuation I/Io is equal to bx, i.e. it is proportional to the distance x.

As shown in FIG. 1, these machines consist essentially of an X-ray source 10 which is associated with a detection device 11, said two elements being arranged with respect to each other in a fixed geometrical relationship so that the body to be examined can be interposed between them. Furthermore, they are supported by a structure (not shown) which can rotate around the body to be examined so as to irradiate the body at different angles. The X-ray source, which is controlled by a device 13, radiates within an angular sector with a width sufficient to illuminate the entire cross section of the body. The detection device 11 has the shape of an annular sector, the length of which is suited to the width of the X-ray beam and consists of a large number of elementary detectors 12, placed beside one another.

To obtain an image of the cross section of the human body through which the X-ray beam flows, the supporting structure of the source 10 and the detection device 11 is made to rotate around the body and the output signals of the elementary detectors 12 are measured so as to be processed appropriately according to known methods in order to extract therefrom an image representing the cross section. For this processing operation, the elementary detectors 12, which are also called channels, are connected to an electronic device 14 which first does a computation of the logarithm of the received signals so as to obtain a signal with an amplitude which is proportional to the attenuation of the X-rays.

Owing to the effect of different phenomena, which shall not be explained herein, the amplitude of this signal for each elementary detector or channel is not proportional to the attenuation or absorption that is actually undergone. Consequently, to cope with this drawback, several methods have been thought of. These methods consist, for example, in sampling the output signals of the channels in the presence of bodies called phantoms the dimensions and absorption coefficients of which are known in such a way as to compute (by logarithmic computations) the attenuations and to compare these measured attenuations with values computed as a function of the dimensions and the absorption coefficients of the phantoms. These comparisons enable the computation of a relationship between the measured values and the values that should have been obtained. This relationship may take the form of files or mathematical formulae for each detection channel.

The phantoms used to perform these so-called calibration measurements are, for example, phantoms of different thicknesses which are introduced in the vicinity of the X-ray source, which implies handling operations at the source to insert and withdraw these phantoms.

The U.S. Pat. No. 4,352,020 proposes the use of circular phantoms 15, 16 and 17, of different diameters, placed at the center of rotation of the supporting structure. This embodiment is close to the conditions of the measurements which will be performed on the body to be examined. This patent also proposes the use of a cone-shaped phantom with a circular section which is moved crosswise with respect to the beam so as to obtain different absorption lengths. With the phantoms described, the measurements are made for a determined position of the supporting structure and for each phantom.

FIG. 2 shows the shape of three response curves 20, 21 and 22 of the attenuation as a function of the position of the channels in the case of measurements on three circular shaped phantoms. The measured values are shown by dots and vary around a mean value which represents the theoretical value in a linear system. These curves can be used as follows: when the measured signal corresponds to a point A, it will be deduced therefore that the linear signal is the point A′ of the mean curve 20. When the measured signal corresponds to a point B located between the curves 20 and 21, the linear signal will be deduced therefrom by interpolation between the curves 20 and 21. This interpolation can be computed according to a linear relationship or, more generally, according to a polynomial relationship.

The curves 23 and 24 of FIG. 3 show the principle of the calibration of a channel in another way. These are curves that describe, in a given channel, the attenuation as a function of the thickness x for measured values (curve 23) and for computed values (plain line 24): in fact, the measured values give points which are connected to one another according to a given relationship, which may be linear or polynomial, so as to obtain a continuous curve. When an attenuation is measured, it corresponds, for example, to the point C of the curve 23 and the linear value corresponding to the point C′ of the curve 24 is deduced therefrom.

The above-mentioned U.S. patent describes an instrument in which the correspondence between the measured and real attenuation values is obtained by a system of files created during the calibrating operation. With respect to the interpolation, the patent proposes linear, cubic or bi-quadratic interpolations but only the linear interpolations are described in detail.

The calibrating methods that have been briefly described above have the major drawback of using several phantoms, and this entails numerous handling operations. Furthermore, these handling operations have to be precise, especially for circular phantoms different centers of which should coincide with the center of rotation of the structure.

It must be noted that the above cited U.S. patent proposes the use of a single phantom which would have the shape shown in FIG. 12 of said patent and proposes making the structure rotate around this phantom: this results in obtaining absorption paths of different lengths depending on the angular position of the structure. However, such an operative procedure is only cited and there is no indication concerning the method or the means for the implementation thereof.

In brief, the purpose of the calibrating methods is to homogenize the response of the channels to one another and to move towards a linear response. To obtain this linear response, a polynomial correction is applied to each channel and this correction is computed, i.e. the coefficients of the polynomial are determined, from measurements made from different values of the absorption path. As such to determine the coefficients of an n order polynomial of a determined channel, it is necessary and sufficient to make (n+1) measurements of different paths for this channel.

In the prior art examples described above, it has been shown that, for example, (n+1) phantoms of different thicknesses or (n+1) circular phantoms of different diameters are used, the values of the thicknesses and diameters being chosen to cover the required dynamic range. This therefore results in numerous handling operations to change from one phantom to another, and these handling operations have to be precise for circular phantoms, the centers of which should coincide with the center of the rotating structure.

SUMMARY OF THE INVENTION

An object of the present invention, therefore, is to apply a calibrating method that uses a single phantom, the position of which is off-centered with respect to the axis of rotation of the scanner.

Another object of the invention is a system to implement said method.

The invention relates to a method for the calibration of an X-ray scanner comprising an X-ray source and a detection device with N detectors or channels borne by a structure which rotates around an axis, said calibration being done by means of a circular phantom, said method comprising the following operations:

positioning said circular phantom, the center of which is placed in a position that is off-centered with respect to the axis of rotation of the scanner, rotating the scanner to make m attenuation measurements $Y_{ij}$ for each order i channel, each measurement corresponding to an angular position $\beta_j$ of the scanner, computing for each measurement $Y_{ij}$, the distance $X_{ij}$ travelled by the radiation in the phantom and computing for each order i channel, the coefficients $A_{ik}$ of the n-degree (n<m) polynomial $P_n^i$ such that:

$$P_n^i(Y_{ij}) = \sum_{k=o}^{k=n} A_{ik} Y_{ij}^k$$

so as to obtain a polynomial approximation of the computed values $X_{ij}$ according to a determined relationship of deviation.

The invention also refers to a system to implement the above-mentioned method, said system comprising:

means for placing at least one circular phantom between the X-ray source and the detection device in a position that is off-centered with respect to the axis of rotation of the rotating structure, means for rotating the scanner to m different angular positions $\beta_j$ close to one another, means for computing the attenuations $Y_{ij}$, undergone by the X-ray radiation in the phantom, from the signals received on the N detectors, means for recording the N values of $Y_{ij}$ for each of the m angular positions $\beta_j$, means for computing from the N.m values of $Y_{ij}$, the off-centered coordinates of the phantom with respect to the axis of rotation of the scanner, means for computing, from the off-centered coordinates, the lengths $X_{ij}$ of the paths of the X-ray radiation in the phantoms as well as the corresponding attenuations $b.X_{ij}$.

means for comparing the values of $Y_{ij}$ with the computed values of the attenuations $b.X_{ij}$ for the same channel and for computing the coefficients $A_{ik}$ of the polynomial approximation and, means for recording said coefficients $A_{ik}$ thus computed, so as to subsequently use them as multiplying coefficients of the attenuations $Y_{ij}$ undergone by the X-radiation in the body of the patient.

BRIEF DESCRIPTION OF THE DRAWINGS

Other features and advantages of the present invention will appear from the following description of a particular embodiment, said description being made with reference to the appended drawings, of which:

FIG. 1 is a schematic diagram of an X-ray scanner showing some circular phantoms used for calibration, according to the prior art;

FIG. 2 is a graph showing various attenuation curves as a function of the position of the detectors or channels and for several values of the diameter of the phantoms;

FIG. 3 is a graph showing the theoretical and measured attenuation curves for a determined channel as a function of the absorption path;

FIG. 4 is a geometrical drawing which enables an understanding of the computation of the X-ray paths for a determined detector when, according to the invention, an off-centered circular phantom is used, and FIG. 5 is a functional diagram of a system for the processing of output signals of detectors so as to implement the method according to the invention.

DESCRIPTION OF PREFERRED EMBODIMENTS

FIGS. 1, 2 and 3, which were used to define the prior art in the preamble, shall not be described again herein.

FIG. 4 gives a schematic but precise view of an X-ray radiation source 30 represented by the point F, a detection device 31 and a circular phantom 32, with a radius R, placed between the first two elements 30 and 31. The source 30 and the detection device 31 are borne by a structure (not shown) which rotates around an axis perpendicular to the plane of the drawing at the point O. The center E of the circular phantom 32 is located at a distance r from the point O, and the segment OE makes an angle $\phi$ with the axis Ox of a system of orthogonal axes x'x-y'y.

The order j position of the supporting structure is defined by the angle $\beta_j$ between the axis Oy and the segment FO (the measurement or viewing position) while the position of an order i detector I of the detection device 31 is defined by the angle $\delta_i$ between FO and FI. This geometrical drawing enables the computation of the path AB called $X_{ij}$ of an X-ray radiation in the off-centered circular phantom element 32 according to the formula:

$$X_{ij} = AB = 2\sqrt{R^2 - \{|FO|\sin\delta_i - r\cos(\Phi - \beta_j - \delta_i)\}^2} \quad (1)$$

The coefficients $A_{ik}$ of the n-order n polynomial of the channel or detector i are computed by minimizing the following quadratic criterion $C_i$ such that:

$$C_i = \sum_{j=1}^{m} \left( \sum_{k=0}^{n} (A_{ik} Y_{ij}^k) - b \cdot X_{ij} \right)^2 \quad (2)$$

a formula wherein:
m is the number of views
$Y_{ij}$ is the signal of the order i channel for the order j view
$A_{ik}$ is the coefficient of the polynomial
$p_n^i$ of the channel i such that:

$$P_n^i(Y_{ij}) = \sum_{k=0}^{k=n} A_{ik} Y_{ij}^k$$

$$P^i(Y) = A_{i,0} + A_{i,1} Y + \ldots A_{i,k} Y^k + \ldots A_{i,n} Y^n$$

The calibration method therefore comprises the following operations:
- positioning a circular phantom, the center of which is offset with respect to the center O of rotation of the radiation source/detector device, the coordinates of E being defined by r and $\Phi$;
- making a number m of measurements $Y_{ij}$ greater than or equal to (n+1) per order i channel if it is desire make an n - order polynomial approximation;
- computing for each measurement $Y_{ij}$, the distance $X_{ij}$ by applying the formula (1);
- computing the coefficients $A_{ik}$ of the polynomial $P_n^i$ by minimizing the quadratic criterion defined the formula (2).

It will be observed that the number m is far greater than (n+1) in order to take the noise of the measurements into account.

To implement this calibration method, the invention proposes a system which shall now be described in relation to FIG. 5. It comprises an analog/digital converter 50 to which are applied the output signals, C1 to CN, of the N detectors or channels of the detection device 31. The N digital codes corresponding to an order j position or view are applied to a logarithm computing circuit 51 which gives a code, representing the attenuation undergone in the standard element, for each channel i and each view j. The N codes resulting from this logarithmic computing operation are applied to a subtraction circuit 52 in which a value REF is subtracted from them, said value REF representing the attenuation undergone by the X-ray radiation outside the phantom, i.e. in the air. This value is obtained by means of a detector called a monitor with a position on the detection device 11 such that it receives the x-ray radiation without attenuation by the phantom.

The codes which result from this subtraction constitute the above-defined measurements $Y_{ij}$. The N values corresponding to an order j view are recorded in two memories, one referenced 53 for the computation of the coefficients $A_{ik}$ according to the calibration method, and the other, referenced 62, to be corrected outside of the calibration operations, by means of the coefficients $A_{ik}$.

With each view corresponding to a different angle $\beta_j$, N values $Y_{ij}$ values are recorded in the memories 53 and 62. The memory 53 is, for example, designed to record the N.m codes corresponding to m views if it is desired to perform an n-order (n<m) polynomial approximation. A device for computing this polynomial approximation comprises the following elements grouped in the box 60. There is a circuit 54 for computing the off-centering of the phantom, namely for computing the polar coordinates r and $\Phi$ of the center E of the phantom. The results of this computation are used in a circuit 55 to compute the distances $X_{ij}$ by applying the formula (1) for the m angular positions $\beta_j$ of the n views. It will be assumed that the computations in the circuits 54 and 55 are done in a digital manner and that, consequently, the distances $X_{ij}$ appear in the form of codes similar to the measurement codes $Y_{ij}$ and are recorded in a memory 61 similar to the memory 53.

The codes contained in the memories 53 and 61 are used in a circuit 58 to compute the polynomial coefficients $A_{ik}$ for each order i channel, by applying the formula (2), in order to obtain a minimum value for $C_i$. These coefficients are recorded in a memory 59 so as to be used in a circuit 63 to correct the values measured in the presence of the patient's body.

The coordinates r and $\Phi$ of the center E of the phantom can be computed in different ways. One of these ways is based on the fact that the strongest attenuation due to the phantom corresponds to a diametrical path, namely a path passing through the center E. Thus, for the order j view, corresponding to $\beta_j=0$ (OF being aligned with the axis Oy), the channel i, where the attenuation is at its maximum, is determined, thus making known the angle $\alpha'$ between the axis Oy and FE. Similarly, the angle $\alpha''$ between the axis Ox' and FE can be determined for the view corresponding to $\beta_j=90°$ (or 180°).

The knowledge of these two angles $\alpha'$ and $\alpha''$, associated with that of the distance FO, enables a computation, by trigonometrical relationships, of the orthogonal coordinates of the center E of the phantom with respect to the axes x'x and y'y. Through a transformation of orthogonal coordinates into polar coordinates, r and $\Phi$ can be obtained.

What is claimed is:

1. A method for the calibration of an X-ray scanner comprising an X-ray source and a detection device with N channels supported by a structure which rotates on an axis about a body under study, said calibration performed by means of a circular phantom, said method comprising the steps of:
   - positioning the circular phantom, the center of which is placed in a position that is off-centered with respect to the axis of rotation of the scanner,
   - irradiating said circular phantom with rays from said X-ray source,
   - moving the scanner to make m measurements of attenuation $Y_{ij}$ for each i channel, each measurement corresponding to an angular position $\beta_j$ of the scanner, computing, for each measurement $Y_{ij}$, the distance $X_{ij}$ travelled by the X-ray radiation in the phantom, computing, for each i channel, the coefficients $A_{ik}$ of integer k of the n-degree polynomial $P_n^i$ such that:

$$P_n^i(Y_{ij}) = \sum_{k=o}^{k=n} A_{ik} Y_{ij}^k$$

so as to obtain a polynominal approximation of the computed values $X_{ij}$, and correcting subsequent measurements made using the scanner using the coefficients $A_{ik}$.

2. A method according to claim 1 wherein the distance $X_{ij}$ is computed by the formula $$2 \sqrt{R^2 - \{|FO|\sin \delta_i - r\cos(\Phi - \beta_j - \delta_i)\}^2}$$

where $\Phi$ = the angle made between the axis Ox, where O is the center of a system of orthogonal axes X'X-Y'Y, and a line segment from the center of the circular phantom to the center of said orthogonal axes; FO is the segment from said X-ray source to said center of said orthogonal axes; R is the radius of the circular phantom; r is the length of said line segment from the center of the phantom to point O; and δ is the angle between the line segment FO and a line segment connecting said X-ray source with an i channel.

3. A method according to claim 1 or 2 wherein the coefficients $A_{ik}$ of the polynomial $P_n^i(Y_{ij})$ are computed by minimizing the mean square deviation:

$$C_i = \sum_{j=1}^{m} \left\{ \sum_{k=o}^{n} (A_{ik} - Y_{ij}^k) - b \cdot X_{ij} \right\}^2$$

wherein b is a coefficient of X-ray absorption depending on the body through which the radiation flows.

4. A system for calibration of an X-ray scanner supported by a structure which rotates on an axis about a body under study, said calibration system comprising:

a scanner including an X-ray source and detection device with N channels, means for placing at least one circular phantom between the X-ray source and the detection device in a position that is off-centered with respect to the axis of rotation of the rotating structure, means for rotating the scanner to m different angular positions $\beta_j$ to close to one another, means for computing the attenuations $Y_{ij}$, undergone by X-ray radiation in the phantom, from signals received by the N channels, means for recording the N values $Y_{ij}$ for each of the m angular positions $\beta j$, means for computing, from the N·m values of $Y_{ij}$, polar coordinates r and $\Phi$ of the off-center phantom with respect to the axis of rotation of the scanner, means for computing, from the off-centered coordinates, the lengths $X_{ij}$ of the paths of the X-ray radiation in the phantom as well as the corresponding attenuations b·$X_{ij}$, means for comparing the values of $Y_{ij}$ with the computed values of the attenuation b·$X_{ij}$ for the same channel and for computing the coefficients $A_{ik}$ of a polynomial approximation, means for recording said coefficients $A_{ik}$ thus computed, so as to subsequently use them as multiplying coefficients of the attenuations $Y_{ij}$ undergone by the X-ray radiation in the body of the patient, and means for correcting subsequent measurements made using the scanner using the coefficients $A_{ik}$.

* * * * *